United States Patent
Bruns et al.

[11] Patent Number: 6,024,566
[45] Date of Patent: Feb. 15, 2000

[54] ABRASIVE CONTAINER FOR GAS-ABRASIVE APPLICATIONS

[75] Inventors: Craig R. Bruns, Danville, Calif.; John J. Bembenek, Burlington, Canada

[73] Assignee: Danville Materials, San Ramon, Calif.

[21] Appl. No.: 08/891,563

[22] Filed: Jul. 11, 1997

[51] Int. Cl.[7] .................................................. A61C 5/14
[52] U.S. Cl. ........................ 433/136; 433/88; 433/116; 128/857; 383/102
[58] Field of Search ................. 433/80, 88, 115, 433/116, 136, 138, 139; 600/119, 121; 128/847, 849, 850, 857, 859, 861, 888; 383/100, 102

[56] References Cited

U.S. PATENT DOCUMENTS

| | | | |
|---|---|---|---|
| 2,637,107 | 5/1953 | Daigle | 433/136 |
| 3,503,497 | 3/1970 | Riely et al. | 383/102 |
| 4,310,118 | 1/1982 | Kisida et al. | 383/102 |
| 4,600,387 | 7/1986 | Ross | 433/136 |
| 4,820,155 | 4/1989 | Sauveur | 433/136 |
| 4,828,491 | 5/1989 | Gray | 433/136 |
| 4,889,490 | 12/1989 | Jenkinson | 433/136 |
| 5,059,036 | 10/1991 | Richison et al. | 383/102 |
| 5,356,292 | 10/1994 | Ho | 433/116 |
| 5,484,283 | 1/1996 | Franetzki | 433/116 |
| 5,522,403 | 6/1996 | Bark et al. | 128/849 |
| 5,547,376 | 8/1996 | Harrel | 433/116 |

FOREIGN PATENT DOCUMENTS 2204933   8/1972   Germany ................ 433/136

*Primary Examiner*—Ralph A. Lewis
*Attorney, Agent, or Firm*—Cooley Godward LLP

[57] ABSTRACT

A device for containing abrasive particles expelled from air-abrasive apparatus and permitting their facile removal without the aid of a vacuum source, while facilitating a relatively unobstructed view of the working area during use. One embodiment disclosed is a device for containing abrasive material expelled by a gas abrasive dental apparatus. The device comprises a flexible puncturable, substantially flat distal sheet comprising one side of the device for isolating a tooth surface to be abraded; a transparent, puncturable, substantially flat proximal sheet comprising the other side of the device; an enclosure for containing the abrasive material. The enclosure is formed by the junction of the proximal sheet and the distal sheet; an enclosure sealing means for permitting access to the enclosure and sealing the enclosure, a filtering means integrated with at least one sheet for permitting the passage of a gas while entrapping the abrasive material, and a rubber dam integrated with the distal sheet, which rubber dam can be secured from within the enclosure around the tooth surface to be abraded by a clamping member. Certain other embodiments of the device can be used for non-dental applications.

39 Claims, 1 Drawing Sheet

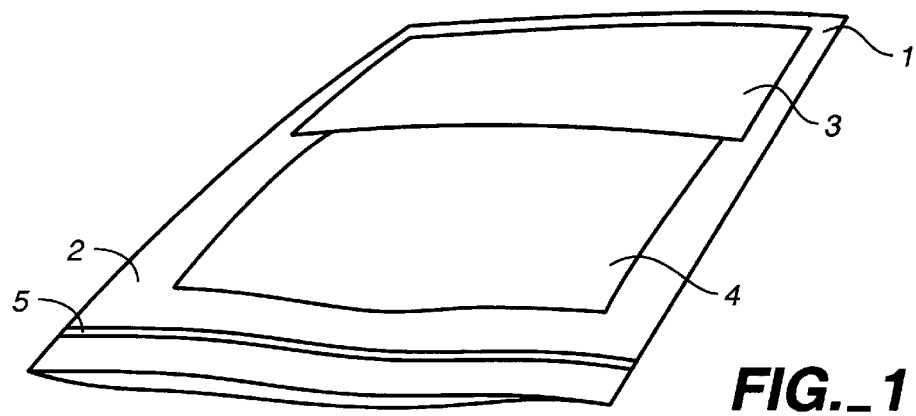
FIG._1
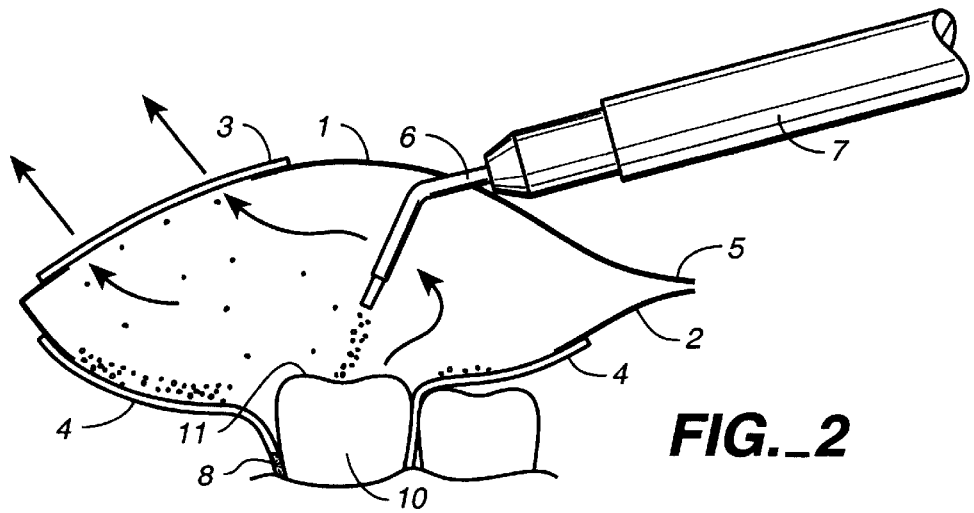
FIG._2
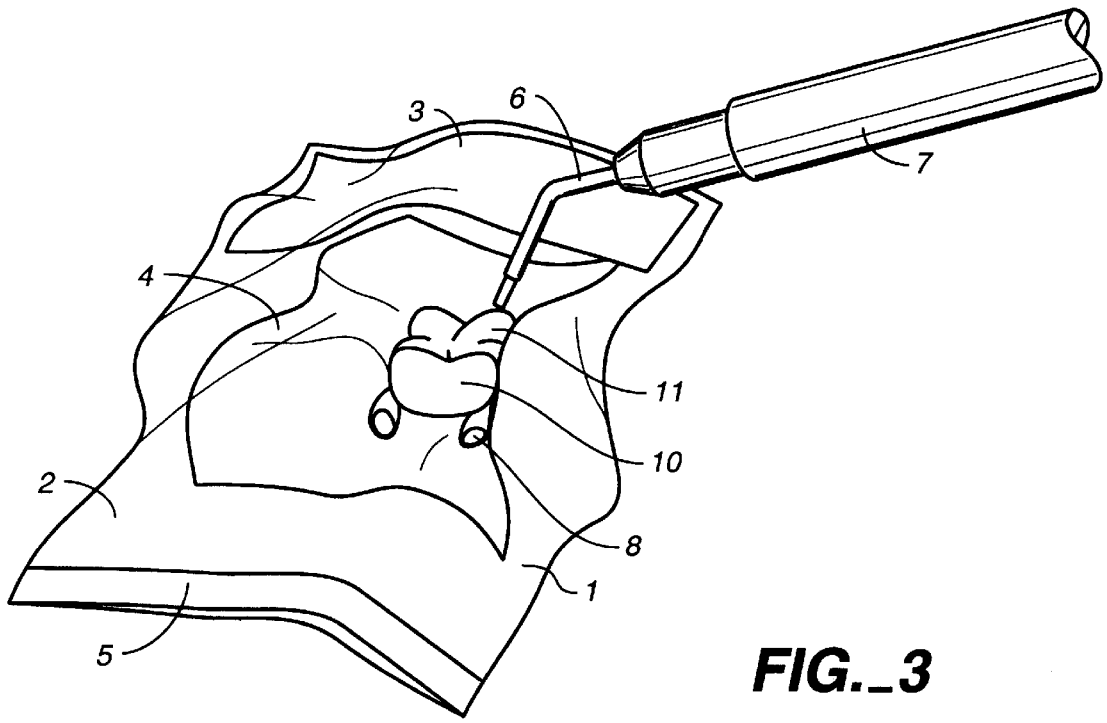
FIG._3

ABRASIVE CONTAINER FOR GAS-ABRASIVE APPLICATIONS

BACKGROUND

1. Field of the Invention

This invention relates to airbrasive devices, and more particularly to devices for containing abrasive materials expelled by a gas-abrasive apparatus. The invention is particularly useful for dental applications.

2. Background of the Invention

The use of sandblasting devices to contact various surfaces has been known for some time. These devices are also known in the art as airbrasive or air-abrasive devices. Such devices vary in size and design depending on the particularly utility desired.

One area where use of these devices has proved advantageous is in the etching or abrading of small surfaces. Devices designed for this use are typically hand held and capable of delivering fine streams of air-abrasive material through narrow nozzles.

A number of decades ago, the use of air-abrasive devices gained favor in the dental art The methods developed were termed "airbrasive techniques" and were designed to supplement the use of traditional dental drills to prepare a tooth for cavity repair, prophylaxis or other methods that required that a portion of the tooth be removed or that required the roughing of a tooth surface. The advantage of using air-abrasive techniques is that the dental patient experiences less trauma to the oral cavity due to the absence of perceptible pressure, vibration, noises created by the contact of a drill to tooth enamel, and heat created by frictional forces. This has resulted in reduced pain, apprehension, and fear by patients.

One disadvantage of the use of air-abrasive dental apparatus is that abrasive materials are dispersed into the oral cavity during use in a relatively uncontrolled fashion, can be inhaled by the patient, and are difficult to remove after a procedure is complete. Another disadvantage is that such particles can be dispersed into the air and create a hygiene problem. Abrasive particles can carry pathogens and blood particles from the mouth and permit those pathogens and blood particles to contact otherwise uncontaminated surfaces.

Somewhat similar disadvantages exist with use of air-abrasive devices in other applications. Often it is desirable to prevent abrasive materials from contacting surfaces proximate to the target surface, from accumulating abrasive material on the target surface area, or from permitting fine abrasive particles from becoming airborne.

Several devices have been developed to affect the dispersion of abrasive particles within the oral cavity. Coston, U.S. Pat. No. 5,197,876 discloses a splatter guard for air polishing dental devices. The guard comprises a bell-shaped flexible cone that is attached to the end of an air-abrasive device and guides abrasive particles towards the surface being treated. Ho, U.S. Pat. No. 5,356,292 discloses a dental sandblasting confiner in the form of a flexible transparent cup. The nozzle of a sandblasting device can be inserted in large opening of the cup which forms a mold around the nozzle. The Ho device contains additional openings for access to a tooth surface and for discharging output. Lokken, U.S. Pat. No. 4,611,992 discloses an anti-splash device that can be attached to a dental tool. The device comprises an inverted U-shaped member with legs for attaching the device to the dental tool. Wright, U.S. Pat. No. 4,850,868 discloses a spray shield comprising a modified tube that can be attached to the end of a dental handpiece. The device is used to direct material dispensed form the handpiece in a controlled fashion so as to minimize the amount of airborne particles.

While the above cited inventions address one or more of the described disadvantages of air-abrasive systems, they are subject to several detrimental limitations. Although minimizing the amount of abrasive material released, by guiding it downward for instance, has certain benefits, it is more preferable to contain a substantial portion of released abrasive material and permit facile removal. Many of the devices in the prior art guide, but do not completely contain abrasive material nor permit easy removal thereof. Other devices that do permit removal of abrasive material are obtrusive and interfere with visualization of the surface to be abraded, making it difficult to perform precise dental procedures. Furthermore, those devices that do permit removal of abrasive material typically rely on a vacuum source to remove that material. Such a vacuum source adds additional expense and can also be intrusive.

Thus, there is a need for a device that can contain a substantial portion of the abrasive material expelled from an air-abrasive device while not obstructing visualization of the surface to be abraded and permitting removal of the abrasive material without the aid of a vacuum source.

OBJECTS OF THE INVENTION

One object of the present invention is to provide a device for containing abrasive material expelled by a gas abrasive apparatus.

Another object of the present invention is to provide a device for containing abrasive material expelled by a gas abrasive apparatus that is capable of containing a substantial portion of expelled abrasive material for easy removal.

Still another object of the present invention is to provide a simple inexpensive device for containing and removing abrasive material expelled by a gas abrasive apparatus without aid of a vacuum source.

Still another object of the present invention is to provide for a method to abrade a surface while containing abrasive material expelled from a gas apparatus.

Still another object of the present invention is to provide a process for making a device for containing material expelled by a gas abrasive apparatus.

Other objects may be apparent to one of ordinary skill upon reading the following specification and claims.

SUMMARY OF THE INVENTION

The present invention provides devices for containing abrasive particles expelled from air-abrasive apparatus and permitting their facile removal without the aid of a vacuum source, while facilitating a relatively unobstructed view of the working area during use.

One aspect of the invention is a device for containing abrasive material expelled by a gas abrasive apparatus. The device comprises a puncturable, substantially flat distal sheet comprising one side of the device for isolating a surface to be abraded; a transparent, puncturable, substantially flat proximal sheet comprising the other side of the device; an enclosure for containing the abrasive material, which enclosure is formed by the junction of the proximal sheet and the distal sheet; an enclosure sealing means for permitting access to the enclosure and sealing the enclosure, and a filtering means integrated with at least one sheet for permitting the passage of a gas while entrapping the abrasive material within the enclosure.

Another aspect of the invention is a device for containing abrasive material expelled by a gas abrasive dental apparatus. The device comprises a flexible puncturable, substantially flat distal sheet comprising one side of the device for isolating a tooth surface to be abraded, a transparent, puncturable, substantially flat proximal sheet comprising the other side of the device; an enclosure for containing the abrasive material, which enclosure is formed by the junction of the proximal sheet and the distal sheet; an enclosure sealing means for permitting access to the enclosure and sealing the enclosure, a filtering means integrated with at least one sheet for permitting the passage of a gas while entrapping the abrasive material, and a rubber dam integrated with the distal sheet, which rubber dam can be secured from within the enclosure around the tooth surface to be abraded by a clamping member.

Still another aspect of the present invention is a method for abrading a surface, particularly a tooth surface, and containing abrasive material. The method comprises abrading the surface with a gas abrasive apparatus in combination with a device (particularly as described above) for containing abrasive material expelled by the gas abrasive apparatus.

Still another aspect of the present invention is a process for making a device for containing abrasive material expelled by a gas abrasive apparatus. The process comprises combining two puncturable, substantially flat sheets so as to form an enclosure, wherein at least one of the sheets is transparent, incorporating a sealing means along at least one of the edges of the enclosure, wherein the sealing means permits access to the enclosure and allows it to be sealed; and incorporating a filtering means into an opening on at least one of the sheets.

Still another aspect of the present invention is a process for making a device for containing abrasive material expelled by a gas abrasive dental apparatus. The process comprises combining two flexible, puncturable, substantially flat sheets so as to form an enclosure, wherein at least one of the sheets is transparent, incorporating a sealing means along at least one of the edges of the enclosure, wherein the sealing means permits access to the enclosure and allows it to be sealed; incorporating a filtering means into an opening on at least one of the sheets, incorporating a rubber dam into at least one of the sheets.

Other aspects of the invention will be apparent to one of ordinary skill in the art upon reading the following specification and appended claims.

BRIEF DESCRIPTION OF THE DRAWINGS

FIG. 1 is a perspective view of the preferred embodiment of the device showing cooperation between a pair of sheets, a filter element, a rubber dam, and a sealing means.

FIG. 2 is a cross-sectional view of the device while in use in a dental application, showing cooperation between the rubber dam and the tooth to be abraded, clamps used to secure the rubber dam around the tooth, the nozzle of the air-abrasive dental apparatus sealingly positioned within the enclosure of the device, and the removal of air from the enclosure wile containing abrasive material.

FIG. 3 is a perspective view of the device while in use in a dental application showing a relatively unobstructed view of the tooth surface to be abraded.

DETAILED DESCRIPTION OF THE PRESENTLY PREFERRED EMBODIMENTS

One aspect of this invention is the device for containing abrasive material expelled by a gas abrasive apparatus. The device comprises a puncturable, substantially flat proximal sheet comprising one side of the device and a puncturable, substantially flat distal sheet comprising the other side of the device. An enclosure for containing the abrasive material is formed by the junction of the proximal sheet and the distal sheet. A resealable enclosure sealing means permits access to the enclosure, and a filtering means, integrated with at least one sheet, permits the passage of a gas while entrapping the abrasive material.

FIG. 1 shows a preferred embodiment of this aspect of the device of the present invention. Generally, the device comprises two square or rectangular sheets joined along at least three edges by a heat seal, gluing or the equivalent thereof to form an enclosure. In the embodiment shown, a proximal sheet 1 has a rectangular filter 3 incorporated into an opening of the sheet 1. A distal sheet 2 has a rubber dam 4 incorporated into the sheet 2. A sealing means 5 is positioned along the remaining edge of the enclosure. The sealing means 5 is preferably resealable.

The sheets 1, 2 can be rigid, flexible, or a combination, but are preferably flexible. At least the proximal sheet 1 must be transparent so that the user can view the surface to the abraded, as further discussed hereinafter. Suitable materials for the construction of the sheets 1, 2 include those materials used to manufacture plastic bags including, but not limited to, polyethylene, polyurethane, polyproplylene, and the like. Others will be apparent to one of ordinary skill in the art. Polyethylene is preferred.

The filter 3 can be constructed of any suitable filter material including porous paper or porous polymeric mesh, such as "TEFLON" mesh. Generally, the filter 3 will be positioned over a cut out rectangular opening on the proximal sheet 1 and will not obstruct visualization of the inside of the enclosure. However, the filter 3 can be positioned on the distal sheet 2, the rubber dam 4, or a portion of both sheets 1, 2. The pore size of the filter must be such as to permit a gas or gas mixture to escape the enclosure while entrapping abrasive particles expelled into the enclosure. One particularly suitable filter consists of a Uniclean™ 350/2 brand filter with 3.5 oz/yd2, 30 cfm/ft2 air permeability 25 millimeters thick. (Midwest Filtration Company, part number FAB-07-15-002P, Fairfield, Ohio).

Rubber dams are well known in the art. Ross, U.S. Pat. No. 4,600,387 discloses a dam frame and dam assembly for use during dental procedures. Sauveur, U.S. Pat. No. 4,820,155 discloses a dam frame for use with endodontic surgery. Gray, U.S. Pat. No. 4,828,491 discloses a unitary preassembled disposable intra-oral rubber dam. Each of these is incorporated herein by reference. Typically, rubber dams are comprised of rubber sheets which can stretch over one or more tooth surfaces and secured with clamps. The rubber dam is usually punctured as required to permit access to one or more tooth surfaces.

The rubber dam 4 of the present invention can be any suitable type available in the art Generally, it will be positioned so as to cover a portion of the distal sheet 2. The rubber dam 4 can be heat melted, glued, or otherwise secured to the inner or outer side of the distal sheet 2.

The sealing means 5 is preferably made of a plastic ridge that integrates into an opposing flexible track, e.g. of the "ZIPLOK" type, but can comprise any suitable sealing means that can be sealed, opened, and resealed. The function of the sealing means is to permit access by an operator to the inside of the enclosure to allow the operator to secure the rubber dam around the tooth surface to perform other manipulations on the tooth surface.

FIG. 2 and FIG. 3 show a preferred embodiment of a method for abrading a surface and containing abrasive material, which method comprises abrading the surface with a gas abrasive apparatus in combination with a device for containing abrasive material expelled by the gas abrasive apparatus. The device shown is for dental use and is inserted into the oral cavity of a patient with the rubber dam 4 placed over the tooth or teeth to be abraded. When in place, parts of the device, including the rubber dam, may extend or protrude beyond the confines of the oral cavity. In the embodiments shown in FIGS. 2 and 3, a hole is punctured in the rubber dam 4 and the rubber dam 4 is stretched over the tooth 10 so as to expose the surface 11 to the inside of the enclosure while forming a seal around the tooth 10. An operator inserts clamps 8 on either side of the tooth 10 from the inside of the enclosure to secure the rubber dam in place. Devices used to clamp rubber dams in place are well known to those of ordinary skill in the dental art and include clamps, dental wedges, and cording material. The operator accesses the inside of the enclosure by unsealing the sealing means 5 to gain access to the inside of the enclosure. The nozzle 6 of a dental air-abrasive apparatus 7 is inserted through a punctured opening on the proximal sheet 1. The puncture is such that a seal is formed around the nozzle 6. When the air-abrasive dental apparatus 7 is in use with the present invention, the air being expelled partially inflates the device of the present invention as shown in FIGS. 2 and 3. As the exposed tooth surface is abraded from within the enclosure, excess abrasive material expelled from the nozzle 6 becomes airborne. The pressure created by the resistance forces of the enclosure forces air to exit through the filter 3. It is understood the terms air and gas as used herein can mean a single gas or a mixture of gasses. Examples include oxygen, nitrogen, argon, carbon dioxide, and atmospheric or industrial air. The abrasive material, having a particle diameter larger than that of the filter pores, is entrapped by the filter and contained within the enclosure. Since the proximal sheet 1 is transparent, the operator can easily observe the abrading procedure. After a dental procedure is complete, the device can be removed from the mouth in a controlled fashion and appropriately disposed of.

Air-abrasive devices are well known to those of ordinary skill in the dental art Herold, U.S. Pat. No. 5,199,229 discloses a hand-held sand blasting device for treating small surface areas. Copending application Danville App. No. 08/562,528 discloses a air-abrasive particle apparatus to abrade a surface with a high level of control. These devices are incorporated herein by reference. Generally the particle size of the abrasive particles will vary in accordance with the needs of the surface being abraded. Larger particles will cause a coarser abrasive pattern and smaller particles will cause a finer pattern. The size may range from about 500 microns to about 10 microns or less.

The device of the present invention can be of varying dimensions depending on the application. In the dental art, the dimensions are dictated by several factors including the number of teeth to be abraded and the size of the oral cavity, that of a child versus an adult, for instance. The dimensions can be symmetrical or non-symmetrical, depending on the particular application. A preferred embodiment of the device will have dimensions ranging from about 1 inch by about 1 inch to about 12 inches by about 12 inches. A more preferred embodiment will range from about 2 inches by about 2 inches to about 6 inches by about 6 inches. A particularly preferred embodiment will be about 3 inches by about 4 inches. The pore size of the filter material should be such as to prevent any abrasive particles from escaping from the enclosure. Typically, pore sizes will be less than about ten microns, preferably less than about one micron. Additionally, the dimensions and placement of the filter can vary. A single filter of a suitable dimension to permit a sufficient amount of gas or air to escape from the enclosure will be adequate. The filter can be rectangular, circular, or other shape and can be placed on either sheet or on the rubber dam itself. One or more filters can be used with the device of the present invention. For example, a plurality of small filters may be placed along appropriate areas of the sheets and rubber dam.

The device and method of the present invention can be used in non-dental applications. Thus, another aspect of this invention is a method for abrading the surface with a gas abrasive apparatus in combination with the device described hereinbefore for containing abrasive material expelled by the gas abrasive apparatus. The method is performed by inserting the nozzle of the gas abrasive apparatus into a puncture on the proximal sheet of the device to abrade an exposed surface within the enclosure and containing the abrasive particle. For example, the device can be used to contain abrasive material used in etching of various surfaces. Preferred embodiments for non-dental applications will depend on the particular application. For example, the dimensions, composition, and configuration of the device can vary depending on the particular non-dental application, such as the etching of antique furniture or the sandblasting of stone surfaces. The sheets can be rigid or flexible. The sheets can vary in dimension ranging from very small to about 5 feet square or greater. All that is required is that at least the nozzle of a sandblasting or air-abrasive device be able to be sealingly inserted into the enclosure, that the working surface be similarly sealingly exposed within the enclosure, and that at least one sheet of the device permit easy visualization of the sandblasting procedure. A rubber dam can be used with non-dental embodiments, but may not be necessary in every application. The materials used to construct the sheets can also vary depending on the level of rigidity desired and the environment of the application, for instance. In some non-dental applications, the sealing means 5 may not be required.

Having completed the description of the apparatus in both its broad aspects and preferred embodiments, one of ordinary skill in the art may identify other aspects and embodiments of the invention that would be apparent and obvious to one upon reading the specification. Such aspects of the invention are meant to be included within the scope of this disclosure and claims.

All references to U.S. patents in this application should be interpreted to incorporate by reference the disclosure of each patent herein.

The subject matter claimed is:

1. A device for containing abrasive material expelled by a gas abrasive apparatus, which device comprises
   a puncturable, substantially flat distal sheet comprising one side of the device for isolating a surface to be abraded, wherein the distal sheet has a rubber dam comprising a rubber sheet integrated therewith, which rubber dam is securable from within the enclosure around the surface to be abraded by a clamping member,
   a transparent, puncturable, substantially flat proximal sheet comprising the other side of the device,
   an enclosure for containing the abrasive material, which enclosure is formed by the junction of the proximal sheet and the distal sheet, an enclosure sealing means capable of permitting access to the enclosure and sealing the enclosure, a filtering means integrated with at least one sheet for permitting the passage of a gas while entrapping the abrasive material within the enclosure.

2. The device of claim 1, wherein the distal sheet is rigid.

3. The device of claim 1, wherein the distal sheet is flexible.

4. The device of claim 1, wherein the filtering means is incorporated into the proximal sheet.

5. The device of claim 1, wherein the filtering means comprises paper.

6. The device of claim 1, wherein the filtering means comprises a polymeric mesh.

7. The device of claim 1, wherein the proximal sheet is flexible.

8. The device of claim 1, wherein the distal sheet has a rubber dam integrated therewith, which rubber dam is securable from within the enclosure around the surface to be abraded by a clamping member.

9. A device for containing abrasive material expelled by a gas abrasive dental apparatus, which device comprises
    a flexible, punctural, substantially flat distal sheet comprising one side of the device for isolating a tooth surface to be abraded,
    a transparent, puncturable, substantially flat proximal sheet comprising the other side of the device,
    an enclosure for containing the abrasive material, which enclosure is formed by the junction of the proximal sheet and the distal sheet,
    an enclosure sealing means capable of being resealed for permitting access to the enclsoure,
    a filtering means integrated with at least one sheet for permitting the passage of a gas while entrapping the abrasive material,
    a rubber dam comprising a rubber sheet integrated with the distal sheet, which rubber dam can be secured from within the enclsoure around the tooth surface to be abraded by a clamping member.

10. The device of claim 9, wherein the filtering means is located on the proximal sheet.

11. The device of claim 9, wherein the filtering means comprises paper.

12. The device of claim 9, wherein the filtering means comprises a polymeric mesh.

13. The device of claim 9, wherein the proximal sheet is flexible.

14. The device of claim 9, wherein the material composition of the sheets is selected from the group of polyethylene, polyurethane, polypropylene, and a combination thereof.

15. A method for abrading a surface and containing abrasive material, which method comprises
    positioning over the surface to be abraded a device for containing abrasive material expelled by a gas abrasive apparatus, which device comprises
        a puncturable, substantially flat distal sheet comprising one side of the device for isolating a surface to be abraded,
        a transparent, puncturable, substantially flat proximal sheet comprising the other side of the device,
        an enclosure for containing the abrasive material, which enclosure is formed by the junction of the proximal sheet and the distal sheet,
        an enclosure sealing means for permitting access to the enclosure and sealing the enclosure,
        a filtering means integrated with at least one sheet for permitting the passage of gas while entrapping the abrasive material,
    sealingly inserting at least the nozzle of the gas abrasive apparatus into a puncture on the proximal sheet to permit the apparatus to abrade an exposed surface within the enclosure,
    abrading the surface with the gas abrasive apparatus in combination with the device for containing abrasive material expelled by the gas abrasive apparatus, and
    collecting the abrasive material in the device.

16. The method of claim 15, wherein the distal sheet is rigid.

17. The method of claim 15, wherein the distal sheet is flexible.

18. The method of claim 16, wherein the filtering means is located on the proximal sheet.

19. The method of claim 16, wherein the filtering means comprises paper.

20. The method of claim 16, wherein the filtering means comprises a polymeric mesh.

21. The method of claim 16, wherein at least one sheet is flexible.

22. The method of claim 16, wherein the distal sheet has a rubber dam integrated therewith, which rubber dam can be secured around the surface to be abraded by a clamping member.

23. The method of claim 15, wherein the material composition of the sheets is selected from the group of polyethylene, polyurethane, polypropylene, and a combination thereof.

24. A method for abrading a tooth surface and containing abrasive material, which method comprises
    positioning over the tooth surface to be abraded a device for containing abrasive material expelled by a gas abrasive apparatus, which device comprises
        a flexible, puncturable, substantially flat distal sheet comprising the other side of the device,
        an enclosure for containing the abrasive material, which enclosure is formed by the junction of the proximal sheet and the distal sheet,
        an enclosure sealing means for permitting access to the enclosure and sealing the enclosure,
        a filtering means integrated with at least one sheet for permitting the passage of gas while entrapping the abrasive material,
        a rubber dam integrated with the distal sheet, which rubber dam can be secured from within the enclosure around the tooth surface to be abraded by a clamping member
    sealingly inserting at least the nozzle of the apparatus into a puncture on the proximal sheet to permit the apparatus to abrade an exposed tooth surface within the enclosures
    abrading the tooth surface with the gas abrasive apparatus in combination with the device for containing abrasive material expelled by the gas abrasive apparatus, and
    collecting the abrasive material in the device.

25. The method of claim 24, wherein the filtering means is located on the proximal sheet.

26. The method of claim 24, wherein the filtering means comprises paper.

27. The method of claim 24, wherein the filtering means comprises a polymeric mesh.

28. The method of claim 24, wherein the proximal sheet is flexible.

29. The method of claim 24, wherein the material composition of the sheets is selected from the group of polyethylene, polyurethane, polypropylene, and a combination thereof.

30. A process for making a device for containing abrasive material expelled by a gas abrasive apparatus, which process comprises combining two puncturable, substantially flat sheets so as to form an enclosure, wherein at least one of the sheets is transparent, wherein a rubber dam comprising a rubber sheet is attached to one of the sheets, incorporating a sealing means along at least one of th edges of the enclosure, wherein the sealing means can be sealed and resealed, and integrating a filtering means over an opening on at least one of the sheets.

31. The process of claim 30, wherein at least one of the sheets is flexible.

32. The process of claim 30, wherein the filtering means comprises paper.

33. The process of claim 30, wherein the filtering means comprises a polymeric mesh.

34. The process of claim 30, wherein the material composition of the sheets is selected from the group of polyethylene, polyurethane, polypropylene, and a combination thereof.

35. The process for making a device for containing abrasive material expelled by a gas abrasive dental apparatus, which process comprises combining two flexible, puncturable, substantially flat sheets so as to form an enclosure, wherein at least one of the sheets is transparent, incorporating a sealing means along at least one of the edges of the enclosure, wherein the sealing means can be sealed and resealed, attaching a filtering means over an opening on at least one of the sheets, attaching a rubber dam to at least one of the sheets.

36. The method of claim 35, wherein the filtering means is located on the proximal sheet.

37. The process of claim 35, wherein the filtering means comprises paper.

38. The process of claim 35, wherein the filtering means comprises a polymeric mesh.

39. The process of claim 35, wherein the material composition of the sheets is selected form the group of polyethylene, polyurethane, polypropylene, and a combination thereof.

* * * * *